(12) United States Patent
Wang

(10) Patent No.: US 12,213,777 B2
(45) Date of Patent: Feb. 4, 2025

(54) METHOD AND SYSTEM FOR MONITORING MOVEMENT

(71) Applicant: BOE Technology Group Co., Ltd., Beijing (CN)

(72) Inventor: Yuan Wang, Beijing (CN)

(73) Assignee: BOE Technology Group Co., Ltd., Beijing (CN)

( * ) Notice: Subject to any disclaimer, the term of this patent is extended or adjusted under 35 U.S.C. 154(b) by 275 days.

(21) Appl. No.: 17/569,179

(22) Filed: Jan. 5, 2022

(65) Prior Publication Data

US 2022/0233099 A1 Jul. 28, 2022

(30) Foreign Application Priority Data

Jan. 26, 2021 (CN) .......................... 202110103275.8

(51) Int. Cl.
  *G06F 3/041* (2006.01)
  *A61B 5/11* (2006.01)
  *G06F 3/01* (2006.01)
  *G16H 40/63* (2018.01)
  *H04W 4/38* (2018.01)

(52) U.S. Cl.
  CPC ................ *A61B 5/11* (2013.01); *G06F 3/011* (2013.01); *G16H 40/63* (2018.01); *H04W 4/38* (2018.02); *A61B 2562/164* (2013.01)

(58) Field of Classification Search
  CPC ...... A61B 5/11; A61B 2562/164; H04W 4/38; G06F 3/011
  See application file for complete search history.

(56) References Cited

U.S. PATENT DOCUMENTS

| | | | |
|---|---|---|---|
| 2012/0071743 A1* | 3/2012 | Todorov ................ | A61B 5/486 600/372 |
| 2016/0287177 A1* | 10/2016 | Huppert ............... | A61B 5/4839 |
| 2018/0143697 A1* | 5/2018 | Kim ........................ | G06F 3/011 |
| 2018/0160940 A1* | 6/2018 | Kim ........................ | A61B 5/45 |
| 2019/0082996 A1* | 3/2019 | Ang ........................ | G06F 3/015 |
| 2020/0163621 A1 | 5/2020 | Connor | |
| 2020/0253539 A1* | 8/2020 | Kaikenger .............. | G01L 1/205 |
| 2020/0397326 A1* | 12/2020 | Rogers ................... | A61B 5/398 |
| 2021/0074006 A1* | 3/2021 | Wang ..................... | G06V 40/176 |

FOREIGN PATENT DOCUMENTS

| | | |
|---|---|---|
| CN | 103417218 A | 12/2013 |
| CN | 103584841 A | 2/2014 |
| CN | 106236098 A | 12/2016 |
| CN | 111616705 A | 9/2020 |

OTHER PUBLICATIONS

CN202110103275.8 first office action.

\* cited by examiner

*Primary Examiner* — Daniel L Cerioni
(74) *Attorney, Agent, or Firm* — IPro, PLLC

(57) ABSTRACT

Disclosed are a method and system for monitoring movement. The system includes: a muscle movement sensor, a movement capturing device and a processing device, wherein the muscle movement sensor is configured to acquire muscle movement information of a moving part of a living body in the case that the muscle movement sensor is fixed onto the moving part; the movement capturing device is configured to acquire whole movement information of the living body; and the processing device is configured to determine a movement parameter of a muscle of the moving part based on the muscle movement information and the whole movement information.

12 Claims, 3 Drawing Sheets

METHOD AND SYSTEM FOR MONITORING MOVEMENT

This application is based on and claims priority to Chinese Patent Application No. 202110103275.8, filed on Jan. 26, 2021 and entitled "SYSTEM AND METHOD FOR MONITORING MUSCLE MOVEMENT ABILITY," the disclosure of which is incorporated herein by reference in its entirely.

TECHNICAL FIELD

The present disclosure relates to the field of biological instruments, and in particular relates to a method and system for monitoring movement.

BACKGROUND

As the medical science has developed towards digitalization, precision, and intelligence in recent years, more and more medical fields need to be supported by the engineering technology. With the increasing attention on medical pertinence and accuracy, a great deal of attention is paid to the monitoring and inspection of specific or single muscle groups, or movement-driven soft tissues of a human body in rehabilitation therapy and movement training.

SUMMARY

Embodiments of the present disclosure provide a method and system for monitoring movement.

According to a first aspect of the embodiments of the present disclosure, a system for monitoring movement is provided. The system includes a muscle movement sensor, a movement capturing device, and a processing device; wherein the muscle movement sensor is configured to acquire muscle movement information of a moving part of a living body in the case that the muscle movement sensor is fixed onto the moving part; the movement capturing device is configured to acquire whole movement information of the living body; and the processing device is configured to determine a movement parameter of a muscle of the moving part based on the muscle movement information and the whole movement information.

In some embodiments, the muscle movement sensor includes a substrate, an information capturing film layer, and an insulative packaging layer which are stacked in sequence; the insulative packaging layer is configured to package the information capturing film layer; and the information capturing film layer is configured to acquire the muscle movement information in the case that the muscle movement sensor is fixed onto the moving part.

In some embodiments, the information capturing film layer includes a plurality of conductive films, a plurality of data lines and a ground line which are disposed on the substrate, the muscle movement sensor further includes a converter, wherein the plurality of conductive films are connected to the plurality of data lines in one-to-one correspondence, and the ground wire and the plurality of data lines are connected to the converter;

the converter is configured to generate a capacitance corresponding to the conductive film connected to each of the plurality of the data lines based on an electric signal on each of the plurality of the data lines and an electric signal on the ground line, and the muscle movement information includes capacitances corresponding to the plurality of conductive films; and the processing device is configured to determine forces applied to the plurality of conductive films based on the capacitances corresponding to the plurality of conductive films, and determine the movement parameter based on the forces applied to the plurality of conductive films and the whole movement information.

In some embodiments, the muscle movement sensor is in accordance with at least one of the following conditions: the substrate, the information capturing film layer and the insulative packaging layer are flexible; the plurality of conductive films are arranged on the substrate in an array; the material of the insulative packaging layer includes an artificial skin material; and the muscle movement sensor is in a shape of an elongated strip, a crescent, or a ring.

In some embodiments, the movement capturing device includes an infrared sensor.

In some embodiments, the whole movement information includes a movement joint diagram of the living body, the movement joint diagram includes a plurality of nodes and lines connecting the nodes, the nodes represent joints of the living body, and the lines represent limbs of the living body.

In some embodiments, the system for monitoring movement further includes a communication device connected to the muscle movement sensor, wherein the communication device is configured to acquire the muscle movement information and transmit the muscle movement information to the processing device.

In some embodiments, the communication device is communicated with the processing device by at least one of the following means: Bluetooth, wireless fidelity, and Zigbee.

In some embodiments, the movement parameter includes at least one of the following parameters: a second force application parameter of a same muscle of the moving part in different actions; a first force application parameter of each of the muscles of the moving part in a same action; and a movement ability parameter of at least one muscle of the moving part, wherein the movement ability parameter is related to at least one of the second force application parameter and the first force application parameter.

In some embodiments, the processing device is connected to a display device, and is further configured to control the display device to display the movement parameter.

In some embodiments, the system for monitoring movement further includes the display device.

In some embodiments, the substrate, the information capturing film layer and the insulative packaging layer are flexible, the plurality of conductive films are arranged on the substrate in an array, a material of the insulative packaging layer includes an artificial skin material, and the muscle movement sensor is in a shape of an elongated strip, a crescent, or a ring;

the movement capturing device includes an infrared sensor, the whole movement information includes a movement joint diagram of the living body, the movement joint diagram includes a plurality of nodes and lines connecting the nodes, the nodes represent joints of the living body, and the lines represent limbs of the living body;

the system for monitoring movement further includes a communication device connected to the muscle movement sensor, the communication device is configured to acquire the muscle movement information and transmit the muscle movement information to the processing device, and the communication device is communicated with the processing device by at least one of: Bluetooth, wireless fidelity, and Zigbee;

the movement parameter includes at least one of the following parameters: a second force application parameter of a same muscle of the moving part in different actions, a first force application parameter of each of the muscles of the moving part in a same action, and a movement ability parameter of at least one muscle of the moving part, wherein the movement ability parameter is related to at least one of the second force application parameter and the first force application parameter; and the system for monitoring movement further includes a display device connected to the processing device, and the processing device is further configured to control the display device to display the movement parameter.

According to a second aspect of the embodiments of the present disclosure, a method for monitoring movement is provided. The method is applicable to any of the systems for monitoring movement according to the first aspect.

The method includes: acquiring muscle movement information of a moving part of a living body by a muscle movement sensor in the case that the muscle movement sensor is fixed onto the moving part; acquiring whole movement information of the living body by a movement capturing device; and determining a movement parameter of a muscle of the moving part by a processing device based on the muscle movement information and the whole movement information.

In some embodiments, the muscle movement sensor includes a substrate, an information capturing film layer, and an insulative packaging layer which are stacked in sequence, and the insulative packaging layer is configured to package the information capturing film layer;

the information capturing film layer includes a plurality of conductive films, a plurality of data lines and a ground line which are disposed on the substrate, the muscle movement sensor further includes a converter, wherein the plurality of conductive films are connected to the plurality of data lines in one-to-one correspondence, and the ground wire and the plurality of data lines are connected to the converter;

acquiring muscle movement information of the moving part of the living body by the muscle movement sensor in the case that the muscle movement sensor is fixed onto the moving part includes: generating a capacitance corresponding to the conductive film connected to each of the plurality of the data lines by the converter based on an electric signal on each of the plurality of the data lines and an electric signal on the ground line in the case that the muscle movement sensor is fixed onto the moving part, the muscle movement information including capacitances corresponding to the plurality of conductive films; and determining a movement parameter of a muscle of the moving part by the processing device based on the muscle movement information and the whole movement information includes: determining, by the processing device, forces applied to the conductive films based on the capacitances corresponding to the plurality of conductive films, and the movement parameter based on the forces applied to the plurality of conductive films and the whole movement information.

In some embodiments, the system for monitoring movement further includes a communication device connected to the muscle movement sensor; and prior to determining the movement parameter of the muscle of the moving part by the processing device based on the muscle movement information and the whole movement information, the method further includes: acquiring the muscle movement information by the communication device; and transmitting the muscle movement information by the communication device to the processing device.

In some embodiments, the processing device is connected to the display device; and in response to determining the movement parameter of the muscle of the moving part by the processing device based on the muscle movement information and the whole movement information, the method further includes: controlling the display device by the processing device to display the movement parameter.

In some embodiments, the system for monitoring movement further includes a communication device connected to the muscle movement sensor, and the processing device is connected to the display device;

prior to determining the movement parameter of the muscle of the moving part by the processing device based on the muscle movement information and the whole movement information, the method further includes: acquiring the muscle movement information by the communication device; and transmitting the muscle movement information by the communication device to the processing device; and upon determining the movement parameter of the muscle of the moving part by the processing device based on the muscle movement information and the whole movement information, the method further includes: controlling the display device by the processing device to display the movement parameter.

According to a third aspect of the embodiments of the present disclosure, a method for monitoring movement is provided. The method is applicable to a processing device in any of the systems for monitoring movement according to the first aspect.

The method includes: acquiring muscle movement information of a moving part of a living body captured by a muscle movement sensor, and whole movement information of the living body captured by a movement capturing device; and determining a movement parameter of a muscle of the moving part based on the muscle movement information and the whole movement information.

According to a fourth aspect of the embodiments of the present disclosure, a storage medium storing a computer program therein is provided. The computer program, when run by a processor, causes the processor to perform any one of the methods according to the third aspect.

In a fifth aspect, an electronic device is provided. The electronic device at least includes: a memory configured to store a computer program therein, and a processor. The computer program, when run by the processor, causes the processor to perform any one of the methods according to the third aspect.

DETAILED DESCRIPTION

For clearer descriptions of the principle, technical solutions and advantages of the embodiments of the present invention, the technical solutions of the embodiments of the present disclosure are described clearly and completely hereinafter with reference to the accompanying drawings. Apparently, the described embodiments are only a part but not all of the embodiments of the present disclosure. All other embodiments obtained by a person skilled in the art based on the described embodiments of the present disclosure without creative efforts shall fall within the protection scope of the present disclosure.

Unless otherwise defined, the technical terms or scientific terms used in the embodiments of the present disclosure shall have the common meanings as understood by a person of ordinary skill in the art to which the present disclosure belongs. The terms "first," "second," and the like in the present disclosure do not indicate any order, quantity, or importance, but are merely used to distinguish different components. The terms "comprise," "include," and the like are intended to mean that the elements or objects before the terms cover the elements or objects or equivalents listed after the terms, without excluding other elements or objects. The terms "connected," "coupled," and the like are not limited to physical or mechanical connections, and may include electrical connection, and the connection may be direct or indirect. The terms "upper," "lower," "top," "bottom," and the like are only used to indicate the relative positional relations; and in response to a change of the absolute position of the described object, the relative positional relationship may also change accordingly.

In order to keep the following description of the embodiments of the present disclosure clear and concise, detailed descriptions of known functions and known components are omitted in the present disclosure.

Figure 1:
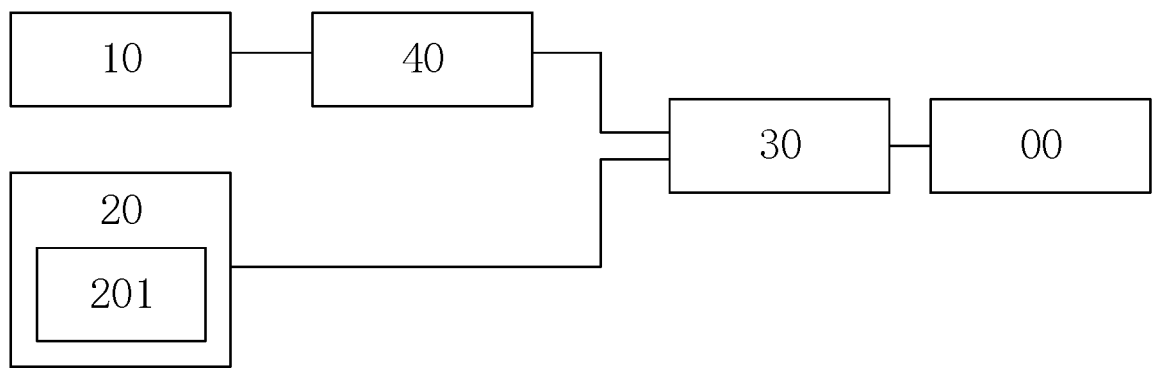
FIG. 1 is a schematic structural diagram of a system for monitoring movement according to an embodiment of the present disclosure.

A system for monitoring movement is provided according to an embodiment of the present disclosure. As shown in FIG. 1, the system includes a muscle movement sensor 10, a movement capturing device 20 and a processing device 30, wherein the muscle movement sensor 10 and the movement capturing device 20 are both connected to the processing device 30.

The muscle movement sensor 10 is configured to acquire muscle movement information of a moving part of a living body (such as a human body or an animal) in the case that the muscle movement sensor 10 is fixed onto the skin of the moving part. The moving part herein refers to the position where a corresponding action or movement is achieved via the contraction, stretching and other deformations of a muscle group in the living body. The muscle group herein includes at least one muscle, such as a single muscle or a muscle combination of multiple muscles. The muscle movement information herein refers to the deformation information of the muscle group during the process that the living body performs an action, and the deformation herein may refer to muscle deformation such as the contraction and stretching. For example, the muscles herein may refer to biceps brachii, latissimus dorsi, or the like.

The movement capturing device 20 is configured to acquire whole movement information of the living body. The whole movement information herein is configured to describe a whole movement situation of the living body in response to an action.

The processing device 30 can acquire the muscle movement information acquired by the muscle movement sensor 10, and the whole movement information acquired by the movement capturing device 20.

In some embodiments, the muscle movement sensor 10 may further be configured to transmit the acquired muscle movement information to the processing device 30, such that the processing device 30 is capable of acquiring the muscle movement information. Exemplarily, the processing device 30 may read a memory of the muscle movement sensor 10 to acquire the muscle movement information. In this case, there may be no need for the muscle movement sensor 10 to transmit the muscle movement information to the processing device 30. Exemplarily, as shown in FIG. 1, the system for monitoring movement may further include a communication device 40. The communication device 40 is connected to the muscle movement sensor 10, and is configured to acquire the muscle movement information and transmit the muscle movement information to the processing device 30.

It should be noted that the communication device 40 herein may include a communication chip. The communication chip that the communication device 40 adopted is compatible with at least one communication protocol such as the Bluetooth communication protocol, the wireless fidelity (Wi-Fi) communication protocol, the Zigbee communication protocol or the like, which are used in hospitals and rehabilitation centers.

Similarly, the movement capturing device 20 may further transmit the acquired whole movement information to the processing device 30. Alternatively, the whole movement information is read by the processing device 30 from the memory of the movement capturing device 20. In this case, there may be no need for the movement capturing device 20 to transmit the whole movement information to the processing device 30. Alternatively, the system for monitoring movement may further include another communication device (not shown in FIG. 1). The communication device is connected to the movement capturing device 20, and is configured to acquire the whole movement information and transmit the whole movement information to the processing device 30.

The processing device 30 is configured to determine a movement parameter of the a muscle of the moving part of the living body based on the acquired muscle movement information and the whole movement information.

In summary, in the system for monitoring movement according to the embodiment of the present disclosure, the muscle movement sensor is capable of acquiring the muscle movement information of the moving part, and the movement capturing device is capable of acquiring the whole movement information of the living body. Furthermore, the processing device determines the movement parameter of the moving part based on not only the whole movement information but also the muscle movement information of the moving part. It can be seen that the processing device can determine the movement parameter of the moving part by combining the movement situation of the moving part with the whole movement situation of the living body. Therefore, the movement parameter determined by the processing device is more accurate.

Figure 2:
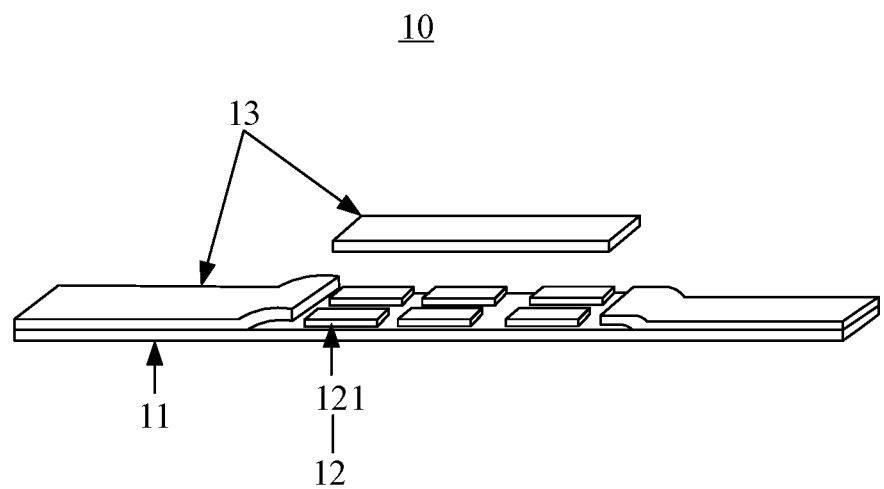
FIG. 2 is a schematic partial structural diagram of a muscle movement sensor according to an embodiment of the present disclosure.

In some embodiments, the muscle movement sensor 10 may be in a form of a sensing film, so as to acquire the muscle movement information of the human body more conveniently. For example, as shown in FIG. 2, the muscle movement sensor 10 includes a substrate 11, an information capturing film layer 12 and an insulative packaging layer 13 which are stacked in sequence. The insulative packaging layer 13 is configured to package the information capturing film layer 12. In the case that the muscle movement sensor 10 is fixed onto the moving part of the living body, the information capturing film layer 12 in the muscle movement sensor 10 is configured to acquire the muscle movement information of the moving part.

Figure 3:
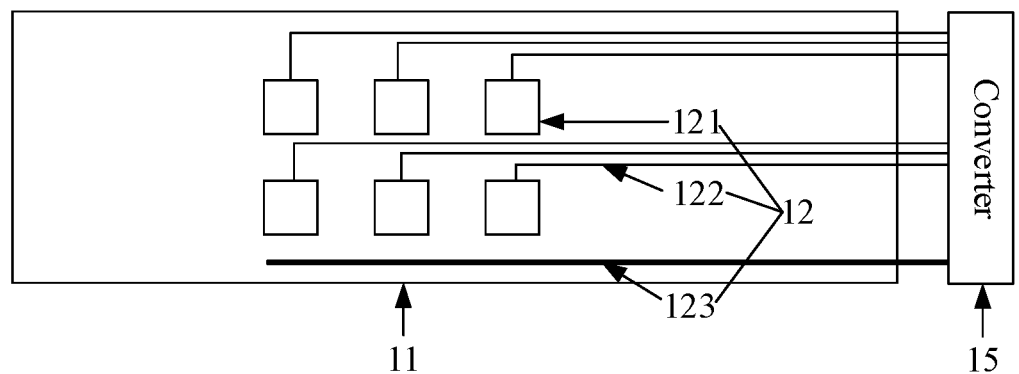
FIG. 3 is a top view of a partial structure of a muscle movement sensor according to an embodiment of the present disclosure.

In an exemplary embodiment, referring to FIG. 2 and FIG. 3 (FIG. 3 is a top view of the substrate and the information capturing film layer shown in FIG. 2), the information capturing film layer 12 includes a plurality of conductive films 121 (such as metal films), a plurality of data lines 122 and a ground line 123 (the data lines 122 and the ground line 123 are not shown in FIG. 2), which are disposed on the substrate 11. The muscle movement sensor 10 further includes a converter 15. The converter 15 may be a single chip microcomputer, a field-programmable gate array (FPGA), or the like. The single chip microcomputer may be an embedded single chip microcomputer (also known as an STM32 single chip microcomputer), or the like.

Figure 4:
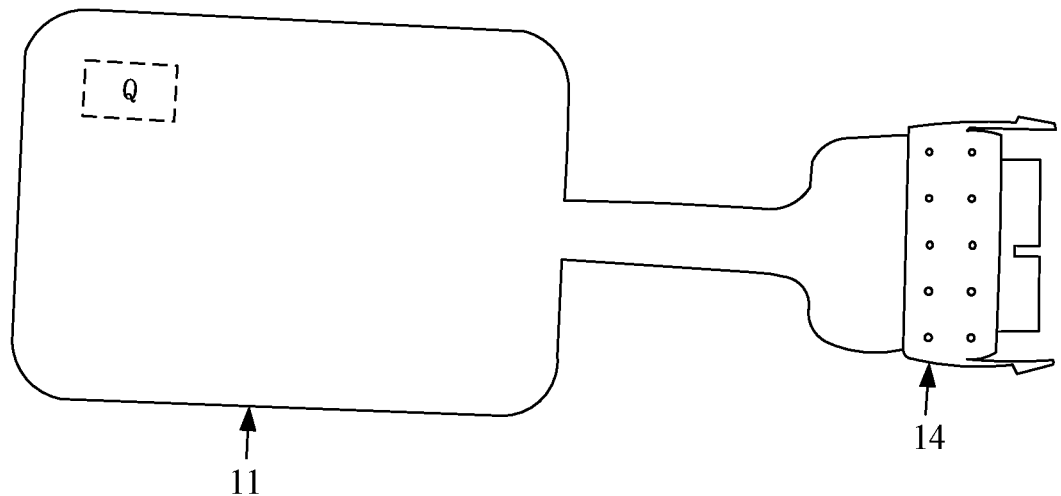
FIG. 4 is a schematic diagram of an output interface of a muscle movement sensor according to an embodiment of the present disclosure.

The plurality of conductive films 121 are connected to the plurality of data lines 122 in one-to-one correspondence, and the ground line 123 and the data lines 122 are all connected to the converter 15. Referring to FIG. 3 and FIG. 4 (FIG. 2 shows a region where the region Q of the muscle sensor is disposed in FIG. 4, and the converter 15 is not shown in FIG. 4). The substrate 11 is provided with an output interface 14. The data lines 122 and the ground line 123 may be all connected to the output interface 14. The converter 15 may also be connected to the output interface 14 and receive electrical signals on the data lines 122 and the ground line 123 via the output interface 14. In some embodiments, in the case that the system for monitoring movement includes a communication device 40, the converter 15 may be connected to the communication device 40.

The converter is configured to generate a capacitance (that is, the capacitance is formed by the conductive film 121 and the ground line 123) corresponding to the conductive film 121 connected to each of the plurality of the data lines 122 based on an electrical signal on each of the plurality of the data lines 122 and an electrical signal on the ground line 123. At this time, the muscle movement information includes capacitances corresponding to the plurality of conductive films 121.

In some embodiments, in the case that the converter is connected to the communication device 40, in response to acquiring the muscle movement information, the converter may first perform analogue-to-digital (A/D) conversion on the muscle movement information, and store the muscle movement information subjected to the A/D conversion locally by, such as, direct memory access (DMA). Then, the converter may transmit the locally stored muscle movement information to the communication device by, for example, a universal synchronous/asynchronous receiver/transmitter (USART).

In the case that the converter is not connected to the communication device 40, if there is a need for the converter to send the muscle movement information to the processing device 30, and the converter may send the muscle movement information to the processing device 30 by sending the muscle movement information to the communication device 40.

Further, in the case that the muscle movement information includes the capacitances corresponding to the plurality of conductive films 121, the processing device 30 is configured to determine a pressure exerted on each of the plurality of conductive films 121 based on the capacitances corresponding to the plurality of conductive films 121, and determine the movement parameter based on the forces applied to the plurality of conductive films 121 and the whole movement information.

It should be noted that in a moving process of the living body, the muscle of a moving part are stretched or compressed. At this time, the degree of extrusion exerted, by the muscle, on the conductive films adjacent to muscle changes, and the forces applied to the conductive films change accordingly. Therefore, the capacitance (the capacitance corresponding to the conductive film) formed by the conductive film and the ground line changes. In the embodiment of the present disclosure, the forces applied to all the conductive films are respectively determined by capturing the capacitances of the conductive films, and these forces are capable of reflecting the movement situation of the muscle of the moving part.

In some embodiments, the substrate 11, the information capturing film layer 12 and the insulative packaging layer 13 are all flexible, for example, made of flexible materials. In this way, the muscle movement sensor 10 is bendable, such that the muscle movement sensor 10 is capable of conveniently acquiring the muscle movement information of the moving part. Not all of these film layers need to be flexible, which is not limited in the embodiment of present disclosure.

In some embodiments, referring to FIG. 3, in the case that the information capturing film layer 12 includes the plurality of conductive films 121, these conductive films 121 may be arranged on the substrate 11 in an array. For example, these conductive films 121 may be arranged between the substrate 11 and the insulative packaging layer 13 in a predetermined fashion. The predetermined fashion herein may be determined based on a shape of the substrate 11 and a distribution region of the muscle of the moving part. For example, conductive films 121 arranged between the substrate 11 and the insulative packaging layer 13 may be in 2 rows and 3 columns, or 3 rows and 3 columns, or 4 rows and 5 columns, or in other configurations.

In addition, it is considered that the muscle movement sensor needs to cover a large area of skin of the moving part in response to acquiring the muscle movement information of the moving part of the living body (also referred to as a subject). Thus, in order to avoid affecting the movement of the living body, the material of the film layer (the insulative packaging layer) proximal to the skin in the muscle movement sensor may include an artificial skin material with elasticity and contractility, such that interference in the movement of the living body can be as little as possible.

Further, the muscle movement sensor is in a shape of an elongated strip, a crescent, a ring, or the like, which is not limited in the embodiment of present disclosure.

The shape and the fixing fashion of the muscle movement sensor may be determined based on different positions of the moving part. For example, in the case of acquiring the muscle movement information of the moving part where the upper arm biceps brachii, deltoid muscle, or the like is located, the muscle movement sensor may be configured in a ring shape and in an armband type, such that the muscle movement sensor is fixed onto an arm in a twisting fashion, shoulder, or other positions. For another example, in the case of acquiring the muscle movement information of the moving part where a latissimus dorsi muscle, an infraspinatus muscle, or the like of a back is located, the muscle movement sensor may be set in a crescent or an elongated strip shape, and the muscle movement sensor may be fixed onto the back or other positions of the human body in a tiled fashion.

Further, referring to FIG. 3, the positions of the conductive films 121 in the information capturing film layer on the substrate 11 are not limited. For example, an example in which the substrate 11 includes a middle region and edge regions on both sides of the middle region is taken for illustration. As shown in FIG. 3, the plurality of conductive films 121 may be arranged in the middle region of the substrate 11, and no conductive film 121 is arranged on the edge regions. Exemplarily, the plurality of conductive films 121 are uniformly arranged on the substrate 11 (this arrangement is not shown in FIG. 3). In this case, the conductive films 121 are arranged in both the middle region and the edge regions of the substrate 11.

In an exemplary embodiment, if it is necessary to acquire the muscle movement information of the moving part (such as an upper arm) where biceps brachii, deltoid muscle, or the like is located, the muscle movement sensor is configured in a ring shape, and the muscle movement sensor is fixed onto the upper arm of the human body in the armband type. In this case, the plurality of conductive films 121 may be arranged in the middle region of the substrate 11, such that the muscle movement information of the upper arm acquired by the muscle movement sensor includes the movement information of the biceps brachii.

In another exemplary embodiment, if it is necessary to acquire the muscle movement information of the moving part (such as a back) where the latissimus dorsi muscle is located, and the muscle movement sensor is configured in a strip shape, such that the muscle movement sensor is fixed onto the back of the human body in the tiled fashion. In this case, the conductive films 121 may be arranged in the middle region and the edge regions of the substrate 11.

In another exemplary embodiment, if it is necessary to acquire the muscle movement information of the moving part (such as a shoulder) where the infraspinatus muscle is located, the muscle movement sensor is configured in a crescent shape, such that the muscle movement sensor is fixed onto the shoulder in the tiled fashion. The conductive films 121 may be arranged in the middle region and the edge regions of the substrate 11.

Further, the muscle movement sensor may be fixed onto the moving part of the living body by a biocompatible adhesive (a bonding agent). Before the muscle movement sensor is fixed onto the moving part of the living body, the surface of the insulative packaging layer of the muscle movement sensor distal from the substrate may be coated with the biocompatible adhesive, and then the muscle movement sensor coated with the biocompatible adhesive may be fixed onto the moving part. In some embodiments, an orthographic projection of a coating position of the biocompatible adhesive on the insulative packaging layer on the substrate may be outside an orthographic projection of the information capturing film layer on the substrate, or may be overlapped with the orthographic projection of the information capturing film layer, which is not limited in the present disclosure.

The biocompatible adhesive needs to be in contact with skin of the moving part; therefore, the biocompatible adhesive should not be harmful to the skin (such as causing no skin allergy). For safety in use, the muscle movement sensor may be cleaned and disinfected with medical alcohol upon each use, and the muscle movement sensor may be fixed onto the moving part by the biocompatible adhesive 12 when being reused.

In the above embodiment, an example in which the information capturing film layer 12 includes the plurality of conductive films 121, the plurality of data lines 122 and the ground line 123 is taken for illustration. In some embodiments, the information capturing film layer 12 may also be practiced in other ways. For example, the information capturing film layer includes a first conductive film, an insulative layer and a second conductive film which are stacked on the substrate 11 in sequence, rather than includes the plurality of conductive films 121, the plurality of data lines 122 and the ground line 123, and both the first conductive film and the second conductive film are connected to a converter. The converter is configured to determine a capacitance formed by the two conductive films and the insulative layer based on electrical signals on the two conductive films. In this case, the muscle movement information includes the capacitance.

Brief introduction is given to the muscle movement sensor 10 above, and the movement capturing device 20 is briefly introduced hereafter.

Referring to FIG. 1, the movement capturing device 20 may include an infrared sensor 201, and for example, the movement capturing device 20 may be an infrared video camera or the like. The movement capturing device 20 may not include the infrared sensor, and for example, the movement capturing device 20 may be a three-dimensional camera or the like.

The movement capturing device 20 may represent the whole movement information of the living body via a movement joint diagram. The movement joint diagram herein is represented by dots and lines. The movement joint diagram includes a plurality of nodes and lines connecting the nodes, wherein the nodes represent joints of the living body and the lines represent limbs of the living body. In this way, the whole movement situation of the living body may be described most concisely and clearly by the movement joint diagram.

In the case that the muscle movement sensor 10 and the movement capturing device 20 are briefly introduced, the processing device 30 is briefly introduced according to the embodiment of the present disclosure.

It can be seen from the above that, the processing device 30 is configured to determine a movement parameter of a muscle of the moving part of the living body based on the muscle movement information and the whole movement information. In some embodiments, upon acquiring the muscle movement information and the whole movement information, the processing device may first perform basic signal processing such as signal amplification, signal filtering and signal decomposition on the muscle movement information and the whole movement information. Then, the processing device 30 may establish a corresponding relationship between actions in the whole movement information and changes (e.g., contraction, stretching, or other changes) of each of the muscles in the muscle movement information. In this way, the processing device 30 may analyze the changes of the muscles of the moving part in movement based on the different actions, so as to acquire the movement ability parameter of the muscles of the moving part.

In some embodiments, the analysis may be performed by, for example, analyzing force application parameters from both lateral and longitudinal aspects.

For example, in the case that a lateral analysis is adopted, the processing device 30 may acquire a first force application parameter of each of the muscles of the moving part of the living body in a same action. Then, the processing device 30 may accurately acquire the movement ability parameter (the movement ability parameter of the muscle may be a score on the movement ability of the muscle) of at least one muscle of the moving part based on the first force application parameters. An abnormal parameter among these movement ability parameters can be found by comparing these movement ability parameters, such that a targeted medical treatment or rehabilitation training plan is designed.

In the case that a longitudinal analysis is adopted, the processing device 30 may acquire a second force application parameter of a same muscle of the moving part of the living body in different actions. Then, the processing device 30 may determine the movement ability parameter of at least one muscle of the moving part based on the second force application parameters. For example, the processing device may acquire force application parameters of a same muscle at different times by combining the muscle movement information and the whole movement information based on a time axis, and determine these force application parameters as the second force application parameters. Furthermore, the processing device 30 may evaluate an effect of rehabilitation therapy or exercise training based on the second force application parameters, such that a next stage of medical treatment or rehabilitation training plan can be designed.

In some embodiments, the processing device 30 may also determine the movement ability parameter of at least one muscle of the moving part based on both the first force application parameter and second force application parameter. It can be seen that the movement ability parameter of the at least one muscle of the moving part is related to at least one of the first force application parameter and the second force application parameter.

Results of the lateral analysis and longitudinal analysis may be displayed by, for example, a display device or the like. For example, referring to FIG. 1, the processing device 30 is connected to the display device 00. The processing device 30 is further configured to control the display device 00 to display the above movement parameters, such as at least one of the second force application parameter, the first force application parameter, and the movement ability parameter.

It should be noted that the system for monitoring movement according to the present disclosure may include the display device, or may not include the display device, which is not limited in the embodiment of present disclosure. The display device may be a desktop computer, a TV, a tablet computer, a mobile phone, a display panel, or any other product or component with a display function.

It can be seen from the above that the muscle movement sensor 10 is closely attached to a muscle of the moving part of the living body to acquire the muscle movement information such as contraction and stretching of the muscle, so as to, for example, monitor the muscle of the moving part. The processing device 30 may further acquire (e.g., acquire in real time) the movement parameter of the muscle of the moving part by comparing and analyzing the muscle movement information and the whole movement information of the living body acquired by the movement capturing device 20, so as to evaluate the effect of the rehabilitation therapy and exercise training on the muscle of the moving part.

The movement parameters of a muscle of the moving part are applicable to rehabilitation training and sports competition training. For example, in rehabilitation training, a rehabilitation state of the muscles may be directly and timely determined based on the movement parameters of the muscles of the moving part, such that the reasonability of design of training actions and the reasonability of a plan for a follow-up training may be determined. For another example, in sports competition training, based on the movement parameters of the muscles of the moving part, a training effect may be effectively determined, which serves as a basis for the plan for the follow-up training, and a physical fatigue state of an athlete is monitored, which serves a basis for real-time changes of training intensity, thereby avoiding overuse-induced sprain and strain or stress-induced sprain and strain.

In the embodiment of the present disclosure, the movement situations of different muscles can be visually compared laterally by capturing the muscle movement information of the moving part and the whole movement information of the living body, such that the abnormal position in the moving part can be accurately determined. In the embodiment of the present disclosure, the movement situations of the muscles of the moving part at different times may also be compared longitudinally, such that the effect of medical treatment or training can be effectively evaluated.

In summary, in the system for monitoring movement according to the embodiment of the present disclosure, the muscle movement sensor is capable of acquiring the muscle movement information of the moving part, and the movement capturing device is capable of acquiring the whole movement information of the living body. Furthermore, the processing device determines the movement parameter of the moving part based on not only the whole movement information but also the muscle movement information of the moving part. It can be seen that the processing device can determine the movement parameter of the moving part by combining the movement situation of the moving part with the whole movement situation of the living body. Therefore, the movement parameter determined by the processing device is more accurate.

In the related art, monitoring devices for rehabilitation training mainly include exoskeleton detecting devices or electromyography capturing and detecting devices. Although these detecting devices for rehabilitation training all use method of detecting joint movement, these detection methods fails to distinguish the movement information of a single muscle in the case that muscle groups work in cooperation. Furthermore, these two detecting devices have great limitations in practical use. The exoskeleton detecting device largely affects movement of a user, and thus cannot monitor the real muscle situation. Therefore, the exoskeleton detecting device are not applicable to sports or trainings. The electromyography capturing and detecting device is generally used in rehabilitation training programs based on electromyography capturing in research papers. The electromyography capturing and detecting device is mainly used for rehabilitation training aimed at symptoms caused by nerve injuries such as stroke and hemiplegia, but is not applicable to symptoms of impaired physical movement abilities such as tendon rupture and muscle tear.

The system for monitoring movement according to the present disclosure can determine the movement parameter of the moving part by combining the movement situation of the moving part with the whole movement situation of the living body. Therefore, the movement parameter determined by the system for monitoring movement is more accurate. In addition, only a few components (e.g., the muscle movement sensor) are required to be fixed on the living body in the system for monitoring movement, and the muscle movement sensor exerts a smaller impact on the movement of the living body. Therefore, the system for monitoring movement according to the present disclosure may be suitable for sports or training, and is capable of monitoring the real muscle situation. Moreover, the system for monitoring movement according to the present disclosure is capable of monitoring the movement parameter of the muscles, and thus the system is applicable to the symptoms of impaired physical movement ability such as tendon rupture and muscle tear.

Figure 5:
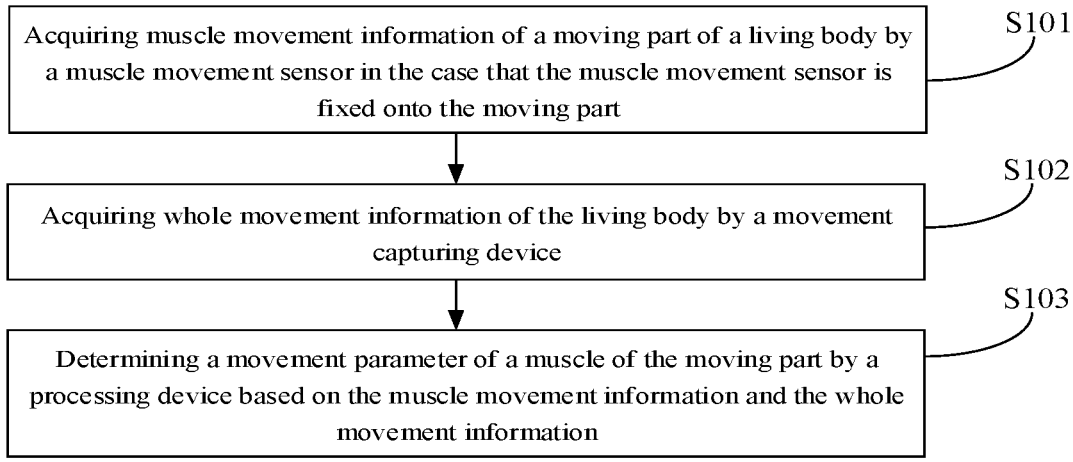
FIG. 5 is a flow chart of a method for monitoring movement according to an embodiment of the present disclosure.

An embodiment of the present disclosure further provides a method for monitoring movement. The method may be applicable to any system for monitoring movement (such as the system for monitoring movement shown in FIG. 1) according to the embodiment of the present disclosure. As shown in FIG. 5, the method for monitoring movement includes the following processes.

In S101, muscle movement information of a moving part of a living body is acquired by a muscle movement sensor in the case that the muscle movement sensor is fixed onto the moving part.

The operation performed by the muscle movement sensor in S101 may refer to the introduction of functions of the muscle movement sensor in the above embodiments, which is not repeated herein.

In S102, whole movement information of the living body is acquired by a movement capturing device.

For the operation performed by the movement capturing device in S102, reference may be made to the introduction of the function of the movement capturing device in the above embodiments, which is not repeated herein.

In S103, a movement parameter of a muscle of the moving part is determined by a processing device based on the muscle movement information and the whole movement information.

For the operation performed by the processing device in S103, reference may be made to the introduction of the function of the processing device in the above embodiments, which is not repeated herein.

In some embodiments, the muscle movement sensor includes a substrate, an information capturing film layer, and an insulative packaging layer which are stacked in sequence. The insulative packaging layer is configured to package the information capturing film layer. The information capturing film layer includes a plurality of conductive films, a plurality of data lines and a ground line which are disposed on the substrate. The muscle movement sensor further includes a converter, the plurality of conductive films are connected to the plurality of data lines in one-to-one correspondence, and the ground wire and the plurality of data lines are connected to the converter.

In S101, in the case that the muscle movement sensor is fixed onto the moving part, a capacitance corresponding to the conductive film connected to each of the plurality of the data lines is generated by the converter based on an electric signal on each of the plurality of the data lines and an electric signal on the ground line; and the muscle movement information includes capacitances corresponding to the plurality of conductive films. In S103, the processing device may determine forces applied to the plurality of conductive films based on the capacitances corresponding to the plurality of conductive films, and the movement parameter based on the forces applied to the plurality of conductive films and the whole movement information.

In some embodiments, the system for monitoring movement further includes a communication device. The communication device is connected to the muscle movement sensor. Prior to S103, the communication device may acquire the muscle movement information and transmit the muscle movement information to the processing device. The system for monitoring movement may not include the communication device. In this case, prior to S103, the muscle movement sensor may directly send the muscle movement information to the processing device, or the processing device may read the muscle movement information from a memory of the muscle movement sensor.

In some embodiments, the processing device is connected to the display device. Upon S103, the processing device may further control the display device to display the movement parameter. For the introduction of the display device, reference may be made to the related introduction in the above embodiments, which is not repeated herein. The processing device may not control the display device to display the movement parameter, which is not limited in the embodiment of the present disclosure.

Figure 6:
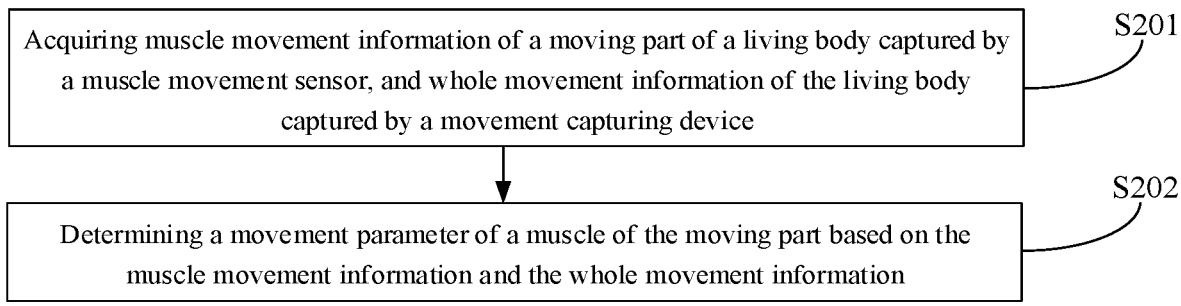
FIG. 6 is a flow chart of another method for monitoring movement according to an embodiment of the present disclosure.

An embodiment of the present disclosure further provides a method for monitoring movement. The method may be applicable to a processing device in any system for monitoring movement (such as the system for monitoring movement shown in FIG. 1) according to the embodiments of the present disclosure. As shown in FIG. 6, the method for monitoring movement includes the following processes.

In S201, muscle movement information of a moving part of a living body captured by a muscle movement sensor and whole movement information of the living body captured by the movement capturing device are acquired.

In S202, a movement parameter of a muscle of the moving part is determined based on the muscle movement information and the whole movement information.

For the method for monitoring movement performed by the processing device, reference may be made to the introduction of the function of the processing device in the above embodiments, which is not repeated herein.

In some embodiments, the muscle movement sensor includes a substrate, an information capturing film layer, and an insulative packaging layer which are stacked in sequence. The insulative packaging layer is configured to package the information capturing film layer. The information capturing film layer includes a plurality of conductive films, a plurality of data lines and a ground line which are disposed on the substrate. The muscle movement sensor further includes a converter, the plurality of conductive films are connected to the plurality of data lines in one-to-one correspondence, and the ground wire and the plurality of data lines are connected to the converter.

In the case that the muscle movement sensor is fixed onto the moving part, a capacitance corresponding to the conductive film connected to each of the plurality of the data lines is generated by the converter based on an electric signal on each of the plurality of the data lines and an electric signal on the ground line; and the muscle movement information includes capacitances corresponding to the plurality of conductive films. In S202, the processing device determines forces applied to the plurality of conductive films based on the capacitances corresponding to the plurality of conductive films, and the movement parameter based on the forces applied to the plurality of conducive films and the whole movement information.

In some embodiments, the system for monitoring movement further includes a communication device. The communication device is connected to the muscle movement sensor. The communication device may acquire the muscle movement information and transmit the muscle movement information to the processing device. In S201, the processing device may receive the muscle movement information from the communication device. The system for monitoring movement may not include the communication device. In this case, in S201, the processing device may receive the muscle movement information from the communication device, or read the muscle movement information from a memory of the muscle movement sensor.

In some embodiments, the processing device is connected to a display device. Upon S201, the processing device may further control the display device to display the movement parameter. For the introduction of the display device, reference may be made to the related introduction in the above embodiments, which is not repeated herein. The processing device may not control the display device to display the movement parameter, which is not limited in the embodiment of the present disclosure.

An embodiment of the present disclosure further provides a storage medium (also called a computer storage medium) storing a computer program therein. The computer program, when run by a processor, causes the processor to perform the method (shown in FIG. 6) performed by the processing device according to any embodiment of the present disclosure.

The storage medium may be configured in a terminal at least including a memory and a processor, and exists in a form of a memory; and specific practice thereof is not repeated herein.

In some embodiments, the storage medium may include, but is not limited to: a USB flash disk, a read-only memory (ROM), a random-access memory (RAM), a removable hard disk, a magnetic disk, an optical disk, or other various media that may store program codes. In some embodiments, the processor performs the method processes described in the above embodiments based on the program codes stored in the storage medium. In some embodiments, for the specific examples in this embodiment, reference may be made to the examples described in the above embodiments and alternative embodiments, which are not repeated herein. Those skilled in the art should understand that each of the foregoing modules or processes of the present disclosure may be practiced with general computing devices, they may be integrated on a single computing device, or distributed in a network composed of a plurality of computing devices. In some embodiments, they may be realized with program codes executable by the computing device, thereby they may be stored in a storage device and run by the computing device. Moreover, in some cases, the processes shown or described may be performed in a different order than the order shown herein, or may be made into an integrated circuit module respectively, or a plurality of modules or processes among them are made into a single integrated circuit module. Thus, the present disclosure is not limited to any specific combination of hardware and software.

Figure 7:
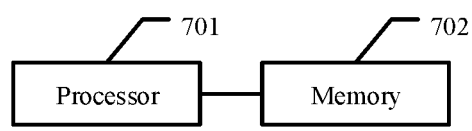
FIG. 7 is a schematic structural diagram of an electronic device according to an embodiment of the present disclosure.

The embodiments of the present disclosure further provide an electronic device. Referring to FIG. 7, the electronic device at least includes: a memory 702 storing a computer program therein, and a processor 701. The computer program, when run by the processor, causes the processor to perform the method (shown in FIG. 6) performed by the processing device according to any embodiment of the present disclosure.

Although the exemplary embodiments have been described herein, scope of the exemplary embodiments includes any and all embodiments based on the present disclosure that have equivalent elements, modifications, omissions, combinations (e.g., solutions of various intersected embodiments), adaptations or changes. The elements in the claims should be broadly interpreted based on the language adopted in the claims, and are not limited to the examples described in the description or during the practice of the present disclosure, and the examples thereof are interpreted as non-exclusive. Therefore, description and the embodiments are intended to be considered as exemplary only, and the true scope and spirit of the present disclosure is indicated by the following claims and the full scope of their equivalents.

The above description is intended to be illustrative but not restrictive. For example, the above examples (or one or more solutions thereof) may be used in combination with each other. For example, a person of ordinary skill in the art may use other embodiments upon reading the above description. In addition, in the foregoing specific embodiments, various features may be grouped together to simplify the present disclosure, which should not be interpreted as an intention that an unclaimed disclosed feature is necessary for any claim. On the contrary, the subject matter of the present disclosure may be less than all features of certain disclosed embodiments. Therefore, the following claims are hereby incorporated into the detailed description as examples or embodiments, in which each claim independently serves as a single embodiment, and it is considered that these embodiments may be combined with each other in various combinations or arrangements.

The scope of the present disclosure should be determined with reference to the appended claims and the full scope of equivalents entitled by these claims. The above embodiments are only exemplary embodiments of the present disclosure, and are not used to limit the present disclosure. The protection scope of the present disclosure is defined by the claims. Those skilled in the art may make various modifications or equivalent substitutions to the present disclosure within the essence and protection scope of the present disclosure, and such modifications or equivalent substitutions should also be regarded as falling within the protection scope of the present disclosure.

It should be noted that the method embodiments and the corresponding device embodiments and system embodiments according to the embodiments of the present disclosure may be referenced with each other, which is not limited in the embodiments of the present disclosure. The order of the processes of the method embodiments according to the embodiments of the present disclosure may be appropriately adjusted, and the processes may be correspondingly increased or decreased as needed. Modified methods which can be easily envisaged by any person skilled in the art within the technical scope disclosed by the present disclosure should be covered by the protection scope of the present disclosure, and thus are not repeated herein.

What is claimed is:

1. A system for monitoring movement, comprising: a muscle movement sensor, a camera, and a processor; wherein the muscle movement sensor comprises a substrate, an information capturing film layer, and an insulative packaging layer which are stacked in sequence, and a converter which is one of a single chip microcomputer and a field-programmable gate array, the information capturing film layer comprises a plurality of conductive films, the converter is connected to each of the conductive films, and the converter is configured to determine a capacitance corresponding to each of the conductive films based on an electrical signal on the conductive film, and the capacitance corresponding to each of the conductive films is one of following capacitances:
a capacitance between a ground line in the information capturing film layer and one of the conductive films; and
a capacitance formed by a first conductive film, an insulative layer in the information capturing film layer and a second conductive film which are stacked on the substrate in sequence, the first conductive film and the second conductive film being two conductive films of the plurality of conductive films;
the converter is further configured to send capacitances corresponding to the plurality of conductive films to the processor;
the processor is configured to determine, in a case that the muscle movement sensor is fixed onto a moving part of a living body so that capacitances corresponding to conductive films adjacent to muscles of the moving part changes with changes in forces which are applied to the conductive films adjacent to the muscles and caused by deformations of the muscles, a pressure exerted on each of conductive films based on the capacitances corresponding to the plurality of conductive film; and
the camera is configured to acquire whole movement information of the living body, the whole movement information comprises a movement joint diagram of the living body, the movement joint diagram comprises a plurality of nodes and lines connecting the nodes, the nodes represent joints of the living body, and the lines represent limbs of the living body.

2. The system according to claim 1, wherein the insulative packaging layer is configured to package the information capturing film layer.

3. The system according to claim 2, wherein the information capturing film layer further comprises a plurality of data lines and a ground line which are disposed on the substrate, wherein the plurality of conductive films are connected to the plurality of data lines in one-to-one correspondence, and the ground line and the plurality of data lines are connected to the converter.

4. The system according to claim 3, wherein the muscle movement sensor is in accordance with at least one of the following conditions:
the substrate, the information capturing film layer, and the insulative packaging layer are flexible;
the plurality of conductive films are arranged on the substrate in an array;
a material of the insulative packaging layer comprises an artificial skin material; and
the muscle movement sensor is in a shape of an elongated strip, a crescent, or a ring.

5. The system according to claim 1, wherein the camera comprises an infrared sensor.

6. The system according to claim 1, further comprising a communication chip connected to the muscle movement sensor, wherein the communication chip is configured to acquire the capacitances corresponding to the plurality of conductive films and transmit the capacitances corresponding to the plurality of conductive films to the processor.

7. The system according to claim 6, wherein the communication chip is communicated with the processor by at least one of: Bluetooth, wireless fidelity, and Zigbee.

8. The system according to claim 3, wherein the substrate, the information capturing film layer, and the insulative packaging layer are flexible, the plurality of conductive films are arranged on the substrate in an array, a material of the insulative packaging layer comprises an artificial skin material, and the muscle movement sensor is in a shape of an elongated strip, a crescent, or a ring;
the camera comprises an infrared sensor;
the system further comprises a communication chip connected to the muscle movement sensor, the communication chip is configured to acquire the muscle movement information and transmit the muscle movement information to the processor, and the communication chip is communicated with the processor by at least one of: Bluetooth, wireless fidelity, and Zigbee.

9. A muscle movement sensor, comprising a substrate, an information capturing film layer, and an insulative packaging layer which are stacked in sequence, and a converter which is one of a single chip microcomputer and a field-programmable gate array, wherein the information capturing film layer comprises a plurality of conductive films, the converter is connected to each of the conductive films, and the converter is configured to determine a capacitance corresponding to each of the conductive films based on an electrical signal on the conductive film, and the capacitance corresponding to each of the conductive films is one of following capacitances:
a capacitance between a ground line in the information capturing film layer and one of the conductive films; and
a capacitance formed by a first conductive film, an insulative layer in the information capturing film layer and a second conductive film which are stacked on the substrate in sequence, the first conductive film and the second conductive film being two conductive films of the plurality of conductive films;
and, the converter is further configured to send capacitances corresponding to the plurality of conductive films to the processor, so that the processor is able to determine, in a case that the muscle movement sensor is fixed onto a moving part of a living body so that capacitances corresponding to conductive films adjacent to muscles of the moving part changes with changes in forces which are applied to the conductive films adjacent to the muscles and caused by deformations of the muscles, a pressure exerted on each of conductive films based on the capacitances corresponding to the plurality of conductive films.

10. The muscle movement sensor according to claim 9, wherein the insulative packaging layer is configured to package the information capturing film layer.

11. The muscle movement sensor according to claim 10, wherein the information capturing film layer further comprises a plurality of data lines and a ground line which are disposed on the substrate, wherein the plurality of conductive films are connected to the plurality of data lines in one-to-one correspondence, and the ground line and the plurality of data lines are connected to the converter.

12. The muscle movement sensor according to claim 11, wherein the muscle movement sensor is in accordance with at least one of the following conditions:
the substrate, the information capturing film layer, and the insulative packaging layer are flexible;

the plurality of conductive films are arranged on the substrate in an array;

a material of the insulative packaging layer comprises an artificial skin material; and the muscle movement sensor is in a shape of an elongated strip, a crescent, or a ring.

* * * * *